United States Patent [19]

Doring et al.

[11] 4,424,818
[45] Jan. 10, 1984

[54] ELECTRICAL LEAD AND INSERTION TOOL

[75] Inventors: John Doring, Spring Lake Park; Rodney Amundson, Lindstrom, both of Minn.

[73] Assignee: Medtronic, Inc., Minneapolis, Minn.

[21] Appl. No.: 349,726

[22] Filed: Feb. 18, 1982

[51] Int. Cl.$^3$ .............................................. A01N 1/00
[52] U.S. Cl. ................................................... 178/784
[58] Field of Search ...................... 128/419 P, 785

[56] References Cited

U.S. PATENT DOCUMENTS

| | | | |
|---|---|---|---|
| 3,737,579 | 6/1973 | Bolduc | 128/418 |
| 3,875,947 | 4/1975 | Jula et al. | 128/418 |
| 3,978,865 | 9/1976 | Trabucco | 128/419 |
| 3,999,555 | 12/1976 | Person | 128/418 |
| 4,010,757 | 3/1977 | Jula et al. | 128/418 |
| 4,058,128 | 11/1977 | Frank et al. | 128/418 |
| 4,066,085 | 1/1978 | Hess | 128/418 |
| 4,144,890 | 3/1979 | Hess | 128/418 |
| 4,146,037 | 3/1979 | Flynn et al. | 128/419 |
| 4,207,903 | 6/1980 | O'Neill | 128/785 |
| 4,235,246 | 11/1980 | Weiss | 128/785 |
| 4,271,846 | 6/1981 | Little | 128/785 |
| 4,280,510 | 7/1981 | O'Neill | 128/784 |
| 4,299,239 | 11/1981 | Weiss et al. | 128/785 |

FOREIGN PATENT DOCUMENTS

WO81/01795  7/1981  PCT Int'l Appl. .

*Primary Examiner*—William E. Kamm
*Attorney, Agent, or Firm*—Reed A. Duthler; John L. Rooney; Joseph F. Breimayer

[57] ABSTRACT

An insertion tool for use with an improved cardiac pacing lead of the type having a barbed electrode and a flexible base pad disposed over the electrode. The insertion tool is provided with a slot for engaging the flexible base pad and a groove for engaging the lead body at an angle to the base pad, exposing the barbed electrode. The lead body is provided with an enlarged diameter segment for frictionally engaging the insertion tool.

14 Claims, 15 Drawing Figures

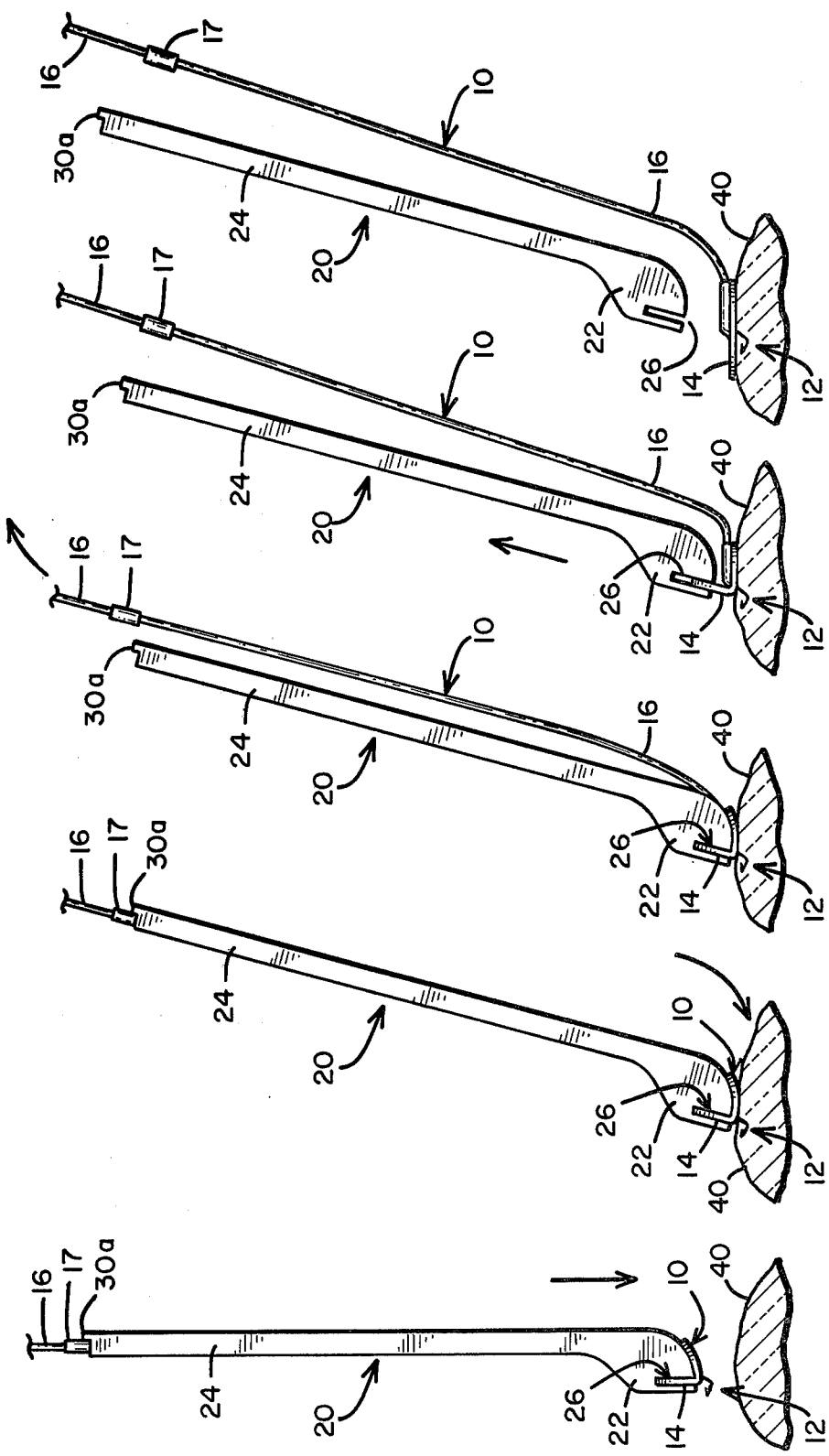

ELECTRICAL LEAD AND INSERTION TOOL

BACKGROUND OF THE INVENTION

1. Field of the Invention

This invention relates to the field of medical electronics and, in particular, to electrical leads and devices for handling electrical leads.

2. State of the Prior Art

An electrical lead including an insulated conductor coil adjacent to a flexible base pad and a barbed electrode spaced adjacent to the base pad and connected to the conductor coil is described in commonly assigned U.S. patent application Ser. No. 115,964 "Myocardial Sutureless Lead" filed by Kenneth B. Stokes on Jan. 28, 1980. The electrode is secured to the heart by gently inserting the tip of the electrode into the myocardial tissue. The flexible base pad limits the implantation depth of the barbed electrode and provides flexibility between the electrode and the lead.

When inserting the lead, it is beneficial to have the flexible base pad bent away from the barbed electrode, allowing the physician to visually locate the barbed electrode when the lead is inserted. Current practice involves the use of a surgical forceps to bend the flexible base back and hold the lead while it is being inserted. The use of a forceps results in extremely high, localized pressures being applied to the lead, increasing the possibility of permanent deformation of the lead. In addition, the present techniques for both grasping the lead and bending back the flexible base have proven to be somewhat awkward, complicating the insertion procedure.

SUMMARY OF THE INVENTION

The purpose of the present invention is to provide an insertion tool for use with a sutureless myocardial unipolar lead of the type having a fixation means and a flexible base means disposed over the fixation means which facilitates attachment of the lead with the body tissue.

According to the preferred embodiment of the present invention, there is an elongated inserter body which has at its distal end a slot for engagement with the flexible base. intersecting this slot is a groove for engagement with the lead body, oriented so that the lead body, when so engaged, is angled relative to the flexible base means, exposing the barbed electrode. The groove extends to the proximal end of the inserter body, allowing the lead body to rest within this groove during insertion.

At the proximal end of the inserter body is a frictional engagement means for frictionally engaging the body of the lead. In its preferred embodiment, the frictional attachment means consists of two projections flanking the groove, which are engaged with an increased diameter segment of the lead body. A slight stretching of the lead is required to engage the increased diameter segment with the projections, and the resulting tension on the lead body maintains this engagement. The combination of the engagement of the flexible base pad with the slot and the engagement of the lead body with the frictional attachment means of the inserter body keeps the lead stably mounted on the insertion tool. Removal of the lead is easily accomplished by slightly stretching the lead body, disengaging the enlarged diameter segment and sliding the inserter body off of the flexible base means.

BRIEF DESCRIPTION OF THE DRAWINGS

Other objects and many of the attendant advantages of this invention will be readily appreciated as the same becomes better understood by reference to the following detailed description when considered in connection with the accompanying drawings wherein:

FIGS. 9a, 9b, 9c, 9d and 9e illustrate the use of the insertion tool shown in FIG. 3 to attach the lead shown in FIG. 1 to body tissue.

DESCRIPTION OF THE PREFERRED EMBODIMENTS

Figure 1:
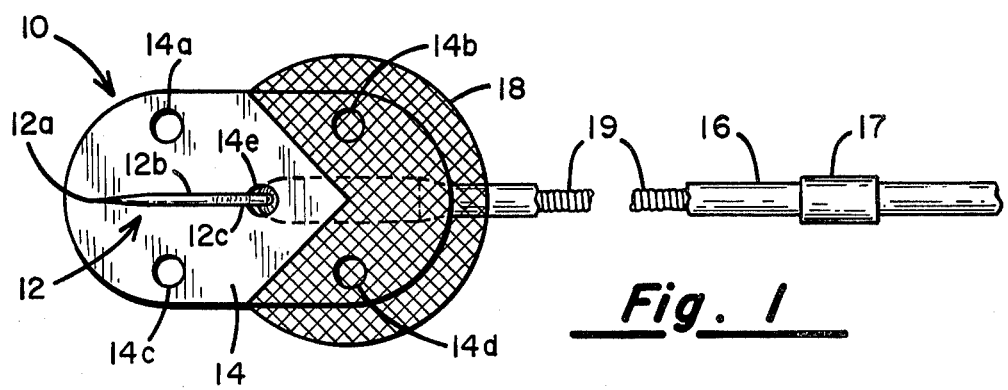
FIG. 1 illustrates a bottom plan view of a sutureless myocardial lead suitable for use with the present invention.

FIG. 1 illustrates a top plan view of a lead of the type suitable for use with the present invention. The myocardial lead 10 includes a forward-facing, in-line barbed electrode 12 on the underside of a flexible base pad 14. The base pad 14 has a plurality of optional suture holes 14a, 14b, 14c and 14d and a centered hole 14e through which barbed electrode 12 protrudes. A surgical mesh 18 having a circumferential portion running approximately 270° from centered hole 14e surrounds centered hole 14e and provides for fibrous ingrowth. The lead body 16 is a polyether urethane elastomer surrounding a multifilar coil 19 of silver/MP35N composite drawn brazed strand (DBS wire), which provides an insulated conductor with stretch and flexibility. Lead body 16 is further comprised of a large diameter segment 17.

Figure 2:
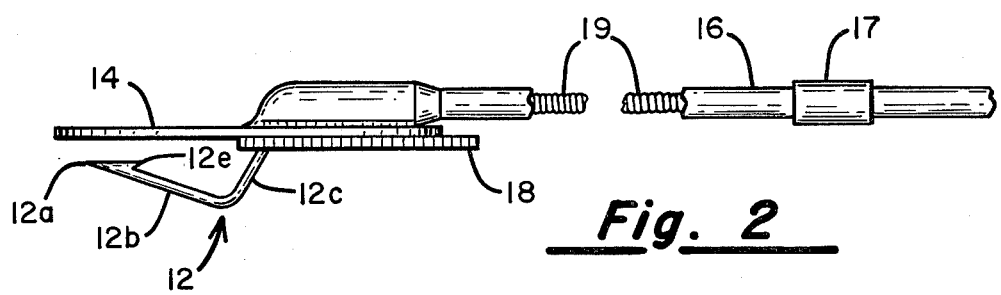
FIG. 2 illustrates a side plan view of a sutureless myocardial lead suitable for use with the present invention.

FIG. 2 illustrates a side plan view of sutureless myocardial lead 10. Barbed electrode 12 includes a tip 12a, a tip shank 12b, and a connecting shank 12c. Barbed electrode 12 is coupled to multifilar coil 19. Base pad 14 and surgical mesh 18 are visible in side view.

Figure 3:
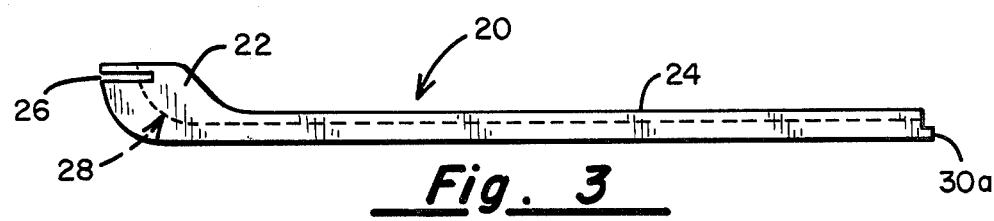
FIG. 3 illustrates a side plan view of a preferred embodiment of the insertion tool of the present invention.

FIG. 3 illustrates a side plan view of the preferred embodiment of the insertion tool of the present invention. The distal end of insertion tool 20 is comprised of inserter head 22. Running from inserter head 22 to the proximal end of insertion tool 20 is elongated handle 24. Inserter head 22 is provided with a slot 26 for engagement with flexible base pad 14 (FIG. 1). Lead body groove 28, indicated by broken line, runs from the distal end to the proximal end of insertion tool 20. Located at the proximal end of insertion tool 20 are projection 30a and projection 30b (not visible) which flank lead body groove 28.

Figure 4:
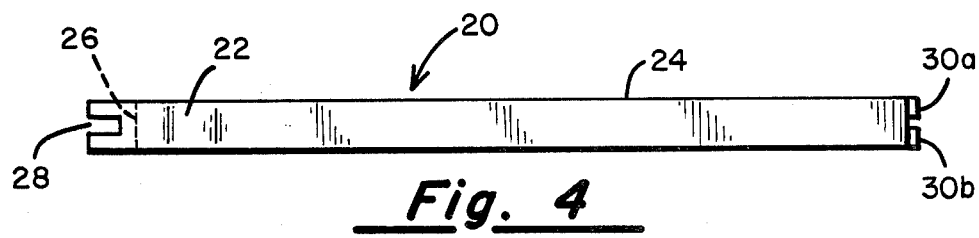
FIG. 4 illustrates a top plan view of the insertion tool shown in FIG. 3.

FIG. 4 illustrates a top plan view of the preferred embodiment of the insertion tool of the present invention. In this view, projections 30a and 30b are both visible at the proximal end of insertion tool 20. Inserter head 22 is seen to be comprised of lead body groove 28 and slot 26 (illustrated by broken line).

Figure 5:
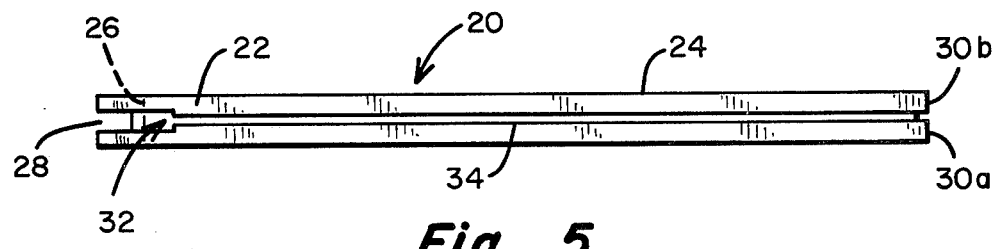
FIG. 5 illustrates a top plan view of the insertion tool shown in FIG. 3.

FIG. 5 illustrates a bottom plan of the preferred embodiment of the insertion tool of the present invention. Lead body slot 28 is seen to narrow at constriction point 32 to a reduced width segment 34. Projections 30a and 30b are seen to flank reduced width section 34 of lead body groove 28. Slot 26 is indicated by broken line.

Figure 6:
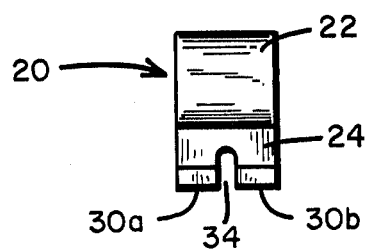
FIG. 6 illustrates an end-on plan view of the proximal end of the insertion tool shown in FIG. 3.

FIG. 6 illustrates an end-on plan view of the proximal end of the insertion tool of the present invention. All numerals correspond to those elements previously delineated in the above figures.

Figure 7:
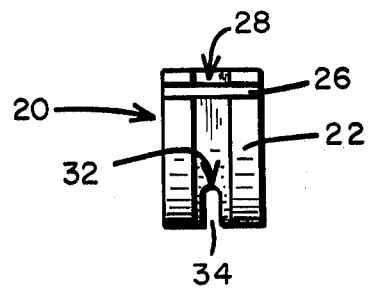
FIG. 7 illustrates and end-on view of the distal end of the insertion tool shown in FIG. 3.

FIG. 7 illustrates an end-on view of the distal end of the preferred embodiment of the insertion tool of the present invention. Slot 26 is seen to intersect lead body groove 28 on inserter head 22. All other numerals correspond to those elements previously delineated in the above figures.

Insertion tool 20 may be made, for example, of a hard plastic material such as Delrin ® which is a trademark of the E. I. DuPont de Nemours Co. for a biocompatible plastic. Preferably, insertion tool 20 should be made of an autoclavible material.

Figure 8A:
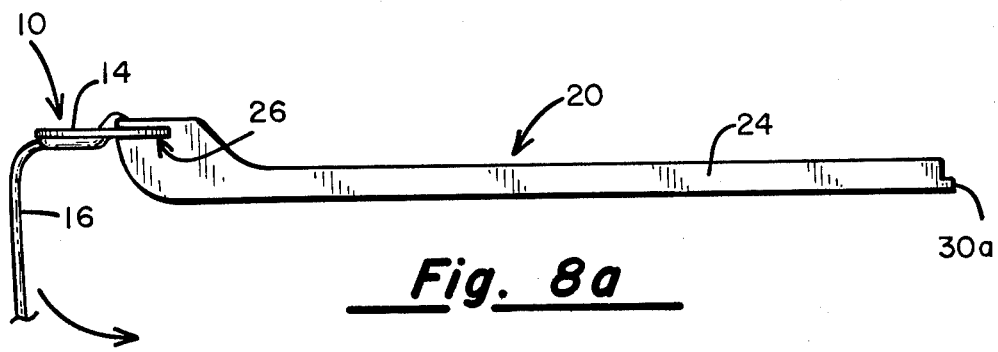
FIGS. 8a, 8b, and 8c illustrate the technique for inserting the lead shown in FIG. 1 into the insertion tool shown in FIG. 3.
Figure 8B:
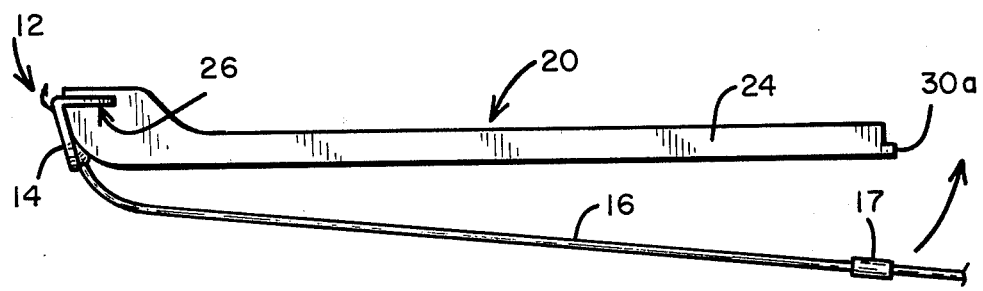
Figure 8C:
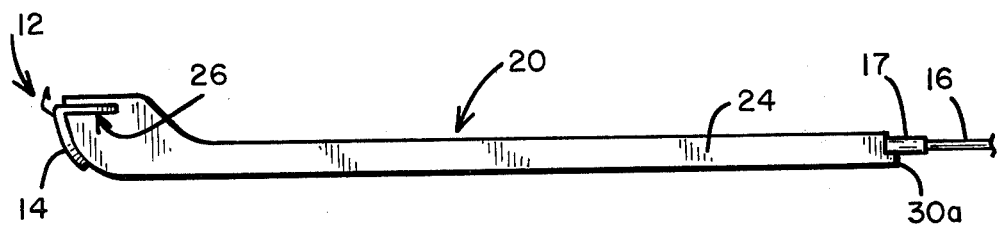

FIGS. 8a, 8b, and 8c illustrate the mounting of myocardial lead 20 on to insertion tool 20. FIG. 8a shows the flexible base pad 14 of lead 10 inserted into slot 26 of insertion tool 20. FIG. 8b shows lead body 16 bent relative to flexible base pad 14 exposing barbed electrode 12. Lead body 16 is stretched slightly so that enlarged diameter portion 17 extends proximal to projections 30a and 30b on the proximal end of insertion tool 20. FIG. 8c shows lead body 16 laid within lead body groove 28 (FIG. 5). Enlarged diameter segment 17 is seen to engage protrusions 30a and 30b. The slight tension on lead body 16 due to its stretching prevents enlarged diameter segment 17 from disengaging from protrusions 30a and 30b. All other numerals correspond to those elements previously delineated in the above drawings.

FIGS. 9a, 9b, 9c, 9d and 9e illustrate the technique of engaging lead 10 with body tissue 40 through use of insertion tool 20. FIG. 9a shows lead 10 mounted on insertion tool 20. Barbed electrode 12 is exposed. FIG. 9b illustrates the engagement of barbed electrode 12 with heart tissue 40. Electrode 12 is engaged using a scooping motion of inserter head 22. FIG. 9c illustrates the disengagement of enlarged diameter segment 17 once barbed electrode 12 has engaged the body tissue. By stretching lead body 16 slightly, enlarged diameter portion 17 is moved proximal to protrusions 30a and 30b so that it may be disengaged from them. FIG. 9d illustrates the removal of flexible base means 14 from slot 26 of inserter head. Tension on lead body 16 is relaxed, allowing it to return to its original length, and insertion tool 20 is slide off of flexible base pad 14 by pulling inserter tool 20 away from body tissue 40. FIG. 9e illustrates lead 10 in its position after engagement with body tissue 40. Flexible base pad 14 has returned to its original configuration, lying flat against body tissue 40. Insertion tool 20 may now be completely removed.

From the foregoing description those skilled in the art will appreciate that numerous modifications may be made of this invention without departing from its spirit. Therefore, it is not intended to limit the breadth of this invention to the embodiment illustrated and described. Rather, it is intended that the breadth of this invention be determined by the appended claims and their equivalents.

What is claimed is:

1. An insertion tool for use with a body implantable lead of the type comprising:
    an elongated lead body having a proximal end and a distal end, further comprised of an elongated insulative sheath and an elongated electrical conductor, having a proximal end and a distal end, fixedly mounted within said elongated insulative sheath;
    means attached to said conductor near the distal end of said lead body for fixing said body implantable lead to body tissue; and
    flexible base means attached to said lead body near the distal end of said lead body which, in a relaxed state, is disposed over said fixation means from at least one direction and which, upon application of a small amount of force, may be bent back exposi said fixation means from said at least one direction;
    said insertion tool comprising an inserter body having:
    first engageable means for releasably engaging said flexible base means; and
    second engageable means for releasably engaging said lead body at an angle relative to said flexible base means when said flexible base means is engaged by said first engageable means for bending back said flexible base means and exposing said fixation means from said at least one direction.

2. An insertion tool according to claim 1 wherein the first engageable means of said inserter body comprises a slot defined therein for engagement with said flexible base means.

3. An insertion tool according to claim 2 wherein the second engageable means of said inserter body comprises a groove defined therein, angled relative to the slot in said inserter body such that when said flexible base means is inserted into the slot in said inserter body and said lead body is engaged with the groove of said inserter body, said flexible base means is bent back, exposing said fixation means from said at least one direction.

4. An insertion tool according to claim 3 wherein said inserter body is further comprised of a frictional engagement means for holding said lead body in the groove of said inserter body.

5. An insertion tool according to claim 4 wherein said inserter body is further comprised of an elongated member.

6. An insertion tool according to claim 5 wherein the groove of said inserter body runs the length of said elongated member.

7. The combination of a body implantable lead and an insertion tool, said body implantable lead comprising:
    an elongated lead body having a proximal end and a distal end, further comprised of an elongated insulative sheath and of an elongated electrical conductor having a proximal end and distal end mounted within said insulative sheath;
    means attached to said conductor near the distal end of said lead body for fixing said body implantable lead;
    flexible base means attached to said lead body near the distal end of said lead body which, in a relaxed state, is disposed over said fixation means from at least one direction and which, upon application of a small amount of force, may be bent back exposing said fixation means from said at least one direction; and said lead body further comprised of a frictional engagement means for engagement with said insertion tool;

said insertion tool comprising an inserter body having:

a first engageable means for releasably engaging said flexible base means;

a second engageable means for releasably engaging said lead body at an angle relative to said flexible base means when said flexible base means is engaged by said first engageable means for bending back said flexible base means and exposing said fixation means from said at least one direction.

8. An implantable lead and insertion tool according to claim 7 wherein the first engageable means of said inserter body comprises a slot therein for engagement with said flexible base means.

9. An implantable lead and insertion tool according to claim 8 wherein the second engageable means of said inserter body comprises a groove defined therein at an angle relative to the slot of said inserter body such that when said flexible base means is engaged with the slot of said inserter body and said lead body is engaged with the groove of said inserter body, said flexible base means is bent back, exposing said fixation means from said at least one direction.

10. An implantable lead and insertion tool according to claim 9 wherein said inserter body is comprised of an elongated member.

11. An implantable lead and insertion tool and lead according to claim 10 wherein the groove of said inserter body runs the length of said elongated member.

12. An implantable lead and insertion tool according to claim 11 wherein said inserter body is further comprised of a third engageable means for engaging said frictional engagement means of said implantable lead.

13. An implantable lead and insertion tool according to claim 7 or claim 8 or claim 9 or claim 10 or claim 11 or claim 12 wherein said frictional engagement means on said lead body comprises an enlarged diameter segment of said lead body.

14. A lead according to claim 12 wherein said third engageable means comprises two protrusions flanking the groove of said inserter body on said elongated member, said protrusions spaced at a distance from one another which is smaller than the diameter of said enlarged diameter portion of said lead body, whereby said protrusions may frictionally engage said enlarged diameter portion of said lead body.

* * * * *

UNITED STATES PATENT AND TRADEMARK OFFICE
CERTIFICATE OF CORRECTION

PATENT NO. : 4,424,818

DATED : January 10, 1984

INVENTOR(S) : John Doring & Rodney Amundson

It is certified that error appears in the above-identified patent and that said Letters Patent are hereby corrected as shown below:

Column 1,
  Line 14, delete "application Ser.";

Line 14, delete "115,964" and insert --4,313,448 for-- therefor;

Column 3,
  Line 55, insert --22-- after "head";

Line 57, delete "slide" and insert --slid-- in place thereof;

Column 4, line 18, "exposi" should be --exposing--.

Signed and Sealed this

Fourth Day of September 1984

[SEAL]

Attest:

GERALD J. MOSSINGHOFF

Attesting Officer  Commissioner of Patents and Trademarks